United States Patent
Fenech et al.

(10) Patent No.: US 11,253,144 B2
(45) Date of Patent: Feb. 22, 2022

(54) SYSTEMS AND METHODS FOR CLEANING A MINIMALLY INVASIVE INSTRUMENT

(71) Applicant: INTUITIVE SURGICAL OPERATIONS, INC., Sunnyvale, CA (US)

(72) Inventors: Carolyn M. Fenech, San Jose, CA (US); Anoop B. Kowshik, Saratoga, CA (US); Stephen J. Blumenkranz, Los Altos, CA (US); Christopher B. Allenby, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 464 days.

(21) Appl. No.: 16/021,326

(22) Filed: Jun. 28, 2018

(65) Prior Publication Data

US 2018/0303328 A1 Oct. 25, 2018

Related U.S. Application Data (62) Division of application No. 13/911,705, filed on Jun. 6, 2013, now Pat. No. 10,039,440.

(Continued)

(51) Int. Cl.
*A61B 1/12* (2006.01)
*A61B 1/04* (2006.01)
(Continued)

(52) U.S. Cl.
CPC .......... *A61B 1/126* (2013.01); *A61B 1/00006* (2013.01); *A61B 1/00009* (2013.01);
(Continued)

(58) Field of Classification Search
CPC ..... A61B 1/126; A61B 1/127; A61B 1/00091; A61B 1/015; A61B 1/00154; A61M 3/0279
See application file for complete search history.

(56) References Cited

U.S. PATENT DOCUMENTS 4,770,163 A * 9/1988 Ono ................... A61B 1/00165
                                                        600/130
5,207,213 A * 5/1993 Auhll ................. A61B 1/00091
                                                        600/104

(Continued)

FOREIGN PATENT DOCUMENTS

EP    1834571 A1    9/2007
EP    2106739 A2    10/2009

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — John P Leubecker
(74) *Attorney, Agent, or Firm* — Haynes and Boone, LLP (57) ABSTRACT

An anatomical probe system includes an elongated flexible body including a channel defined by a wall, an operational component, a support member, an image obstruction detector, and a fluid director. The support member comprises a curved wall having a portion sized to fit within the channel and a frame shaped to retain the operational component. A frame wall is coupled to the curved wall such that the frame wall and the portion of the curved wall form an enclosed interior channel. The frame wall overlaps the portion of the curved wall in an axial direction such that a plane transverse to the axis intersects both the frame wall and the portion of the curved wall. The image obstruction detector is config- (Continued)

ured to detect an obstruction of the operational component and initiate a cleaning routine. The fluid director is configured to direct the fluid toward the operational component.

19 Claims, 9 Drawing Sheets

Related U.S. Application Data (60) Provisional application No. 61/658,305, filed on Jun. 11, 2012.

(51) Int. Cl.
*A61B 1/015* (2006.01)
*A61B 17/00* (2006.01)
*A61M 13/00* (2006.01)
*A61M 3/02* (2006.01)
*A61B 1/00* (2006.01)
*A61M 1/00* (2006.01)
*A61B 34/30* (2016.01)

(52) U.S. Cl.
CPC .......... *A61B 1/00091* (2013.01); *A61B 1/015* (2013.01); *A61B 1/04* (2013.01); *A61B 17/00234* (2013.01); *A61M 1/84* (2021.05); *A61M 3/0279* (2013.01); *A61M 13/003* (2013.01); *A61B 1/00154* (2013.01); *A61B 34/30* (2016.02); *A61M 2202/0225* (2013.01)

(56) References Cited

U.S. PATENT DOCUMENTS

| | | | |
|---|---|---|---|
| 5,313,934 A * | 5/1994 | Wiita | A61B 1/00091 600/109 |
| 5,630,795 A | 5/1997 | Kuramoto et al. | |
| 5,647,840 A * | 7/1997 | D'Amelio | A61B 1/00091 600/169 |
| 5,685,823 A | 11/1997 | Ito et al. | |
| 5,725,474 A | 3/1998 | Yasui et al. | |
| 5,725,477 A | 3/1998 | Yasui et al. | |
| 6,126,592 A | 10/2000 | Proch et al. | |
| 6,447,445 B1 | 9/2002 | Hirano | |
| 6,595,915 B2 | 7/2003 | Akiba | |
| 6,638,214 B2 | 10/2003 | Akiba | |
| 8,047,215 B1 * | 11/2011 | Sasaki | A61B 1/00091 134/95.2 |
| 8,419,624 B2 | 4/2013 | James | |
| 2006/0069306 A1 * | 3/2006 | Banik | A61B 1/0008 600/118 |
| 2006/0111612 A1 | 5/2006 | Matsumoto | |
| 2006/0173244 A1 | 8/2006 | Boulais et al. | |
| 2007/0135682 A1 * | 6/2007 | Miyagi | A61B 1/00096 600/129 |
| 2007/0229954 A1 * | 10/2007 | Bral | A61B 1/126 359/509 |
| 2007/0249907 A1 | 10/2007 | Boulais et al. | |
| 2008/0214895 A1 | 9/2008 | Campos | |
| 2008/0281293 A1 * | 11/2008 | Peh | A61B 1/0051 604/523 |
| 2009/0253964 A1 * | 10/2009 | Miyamoto | A61B 1/126 600/157 |
| 2009/0253965 A1 | 10/2009 | Miyamoto | |
| 2009/0299135 A1 | 12/2009 | Spivey | |
| 2010/0022841 A1 * | 1/2010 | Takahashi | G02B 7/025 600/162 |
| 2010/0240950 A1 | 9/2010 | Heimberger | |
| 2010/0256448 A1 | 10/2010 | Smith et al. | |
| 2011/0046446 A1 * | 2/2011 | Hirayama | A61B 1/05 600/158 |
| 2011/0092769 A1 * | 4/2011 | Kokubo | A61B 1/127 600/109 |
| 2011/0237880 A1 * | 9/2011 | Hamel | A61B 1/00009 600/104 |
| 2012/0289858 A1 | 11/2012 | Ouyang et al. | |
| 2013/0331730 A1 | 12/2013 | Fenech et al. | |
| 2014/0148644 A1 | 5/2014 | Levi et al. | |

FOREIGN PATENT DOCUMENTS

| | | |
|---|---|---|
| JP | H11151198 A | 6/1999 |
| JP | 2002058632 A | 2/2002 |
| JP | 2010115428 A | 5/2010 |
| JP | 2010246633 A | 11/2010 |
| WO | WO-02100238 A2 | 12/2002 |
| WO | WO-2011030679 A1 | 3/2011 |

* cited by examiner

SYSTEMS AND METHODS FOR CLEANING A MINIMALLY INVASIVE INSTRUMENT

CROSS-REFERENCE TO RELATED APPLICATIONS

This application is a Divisional of U.S. patent application Ser. No. 13/911,705 filed Jun. 6, 2013 (issued as U.S. Pat. No. 10,039,440), which claims the benefit of and priority to U.S. Provisional Application No. 61/658,305 filed Jun. 11, 2012, both of which are incorporated by reference herein in their entireties.

FIELD

The present disclosure is directed to systems and methods for minimally invasive surgery, and more particularly to systems and methods for cleaning a minimally invasive instrument.

BACKGROUND

Minimally invasive medical techniques are intended to reduce the amount of tissue that is damaged during diagnostic or surgical procedures, thereby reducing patient recovery time, discomfort, and harmful side effects. Such minimally invasive techniques may be performed through one or more of a patient's natural orifices (e.g., ear, nose, mouth, urethra, vagina, anus) or through one or more surgical incisions. Clinicians insert surgical instruments through these natural orifices or incisions to reach a target tissue location. To reach the target tissue location, the minimally invasive surgical instruments may navigate natural or surgically created connected passageways in anatomical systems, such as the pulmonary, gastro-intestinal, urinary, circulatory, lymphatic, and nervous systems, or the like. To allow a surgeon to visualize the passageways, often an endoscopic probe is fed through the passageways to capture and return images. As the endoscopic probe is advanced, body matter, such as blood, tissue, or mucus, accumulates on the end of the probe and obstructs the view of the passageways. Typically, a surgeon must interrupt the procedure to remove the probe for cleaning. This external cleansing practice is time consuming and increases the risk of damaging patient tissue with repeated insertions of the probe. Improved systems and methods are needed for cleaning endoscopic probes in vivo.

SUMMARY

The embodiments of the invention are summarized by the claims that follow the description.

In one embodiment, an anatomical probe system comprises an elongated flexible body and an operational component extending within a channel of the flexible body. The system also comprises a support member at a distal end of the elongated flexible body. The support member includes a fluid director adapted to direct a fluid from the channel toward the operational component.

In another embodiment, a method of operating an anatomical probe system comprises providing an elongated flexible body including a channel and providing an operational component extending within the channel of the flexible body. The method further comprises providing a support member at a distal end of the flexible body. The support member includes a fluid director. The method also comprises conveying fluid through the channel and into contact with the fluid director to direct the fluid toward the operational component.

In another embodiment, an endoscopic probe system comprises an elongated flexible body including a channel and a camera component extending within the channel. The system also comprises a support member coupled to a distal end of the elongated flexible body. The support member includes an outer (e.g., cylindrical) wall, an optional frame affixed within the outer wall and adapted to position the camera component within the cylindrical wall, and a fluid director extending from the outer wall. The fluid director is adapted to direct a fluid from the channel toward the camera component.

In another embodiment, a method comprises providing an anatomical probe system. The probe system includes an image capture instrument. The method also comprises detecting an obstruction of a view of an image capture instrument and initiating a cleaning routine of the image capture instrument. The method also comprises detecting a decreased obstruction of the view of the image capture instrument and terminating the cleaning routine.

In another embodiment, a minimally invasive surgical system comprises an elongated body defining a channel in which an image capture instrument or other heat-generating instrument is positioned. The surgical system is further configured to flow liquid (e.g., water or saline) or gas (e.g., nitrogen or carbon dioxide) through the channel and over and/or through the image capture instrument to provide cooling for the instrument. In some embodiments, cleaning liquid for the image capture instrument (e.g., for cleaning/clearing the image capture instrument lens), or insufflation gas for use during the procedure, can be used for this cooling purpose in addition to any other cleaning/insufflation activity.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

Figure 1:
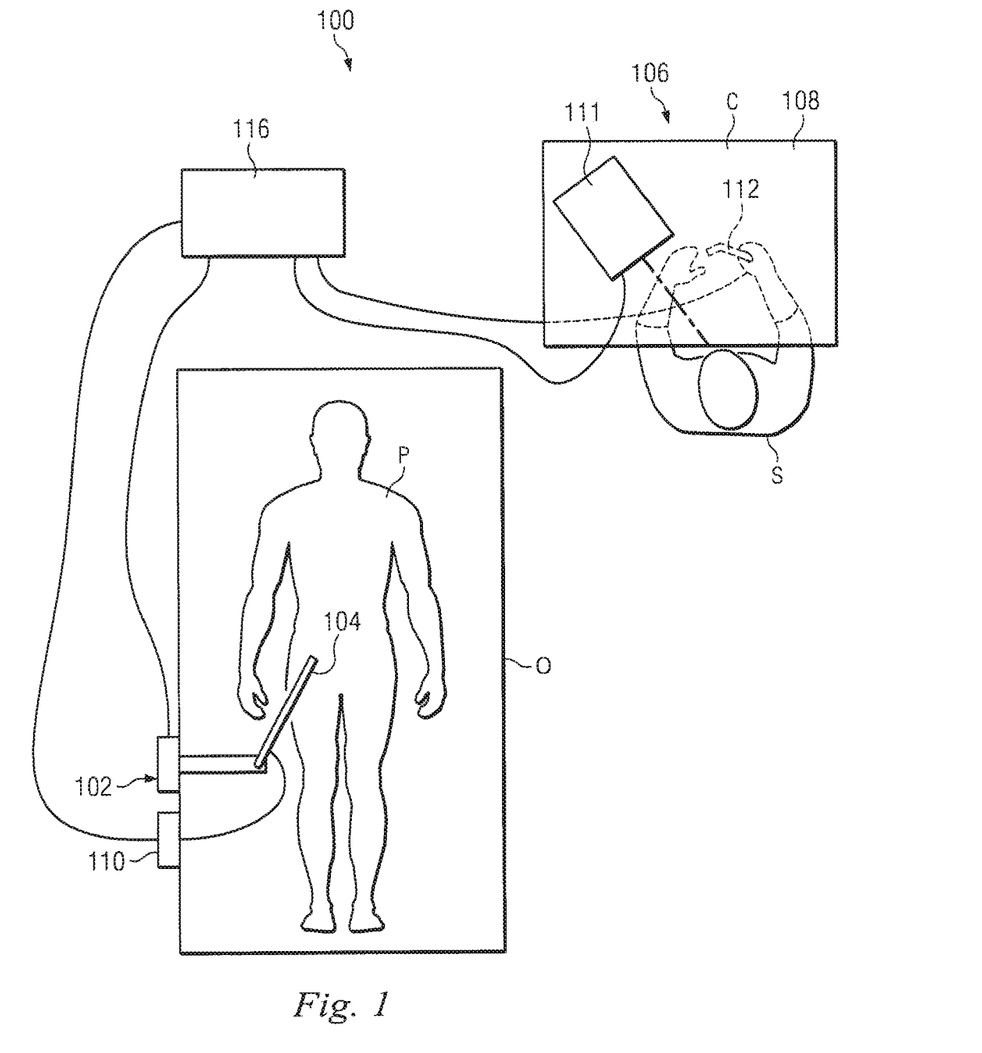
FIG. 1 is a diagrammatic top view of robotic surgical system, in accordance with embodiments of the present disclosure.

Referring to FIG. 1 of the drawings, a robotic surgical system is generally indicated by the reference numeral 100. As shown in FIG. 1, the robotic system 100 generally includes a slave surgical manipulator assembly 102 for operating a surgical instrument 104 in performing various procedures on the patient P. The assembly 102 is mounted to or near an operating table O. A master assembly 106 allows the surgeon S to view the surgical site and to control the slave manipulator assembly 102.

The master assembly 106 may be located at a surgeon's console C, which is usually located in the same room as operating table O. However, it should be understood that the surgeon S may be located in a different room or a completely different building from the patient P. Master assembly 106 generally includes an optional arm or hand support 108 and one or more control device(s) 112 for controlling the manipulator assembly 102. The control device(s) 112 may include any number of a variety of input devices, such as joysticks, trackballs, data gloves, trigger-guns, hand-operated controllers, voice recognition devices, body motion or presence sensors, or the like. In some embodiments, the control device(s) 112 will be provided with the same degrees of freedom as the associated surgical instruments 104 to provide the surgeon with telepresence, or the perception that the control device(s) 112 are integral with the instruments 104 so that the surgeon has a strong sense of directly controlling instruments 104. In other embodiments, the control device(s) 112 may have more or fewer degrees of freedom than the associated surgical instruments 104 and still provide the surgeon with telepresence. In some embodiments, the control device(s) 112 are manual input devices which move with six degrees of freedom. Input devices may also include additional degrees of freedom, such as an actuatable handle, lever, or button, for actuating instruments (for example, for closing grasping jaws, applying an electrical potential to an electrode, delivering a medicinal treatment, or the like).

In alternative embodiments, the robotic system may include more than one slave manipulator assembly and/or more than one master assembly. The exact number of manipulator assemblies will depend on the surgical procedure and the space constraints within the operating room, among other factors. The master assemblies may be collocated, or they may be positioned in separate locations. Multiple master assemblies allow more than one operator to control one or more slave manipulator assemblies in various combinations. To simplify the following description, however, inventive aspects are described in terms of a single manipulator assembly and surgical instrument.

A visualization system 110 may include an endoscope system such that a concurrent (real-time) image of the surgical site is provided to surgeon console C. The concurrent image may be, for example, a two- or three-dimensional image captured by an endoscopic probe positioned within the surgical site. In this embodiment, the visualization system 110 includes endoscopic components that may be integrally or removably coupled to the surgical instrument 104. In alternative embodiments, however, a separate endoscope attached to a separate manipulator assembly may be used to image the surgical site. Alternatively, a separate endoscope assembly may be directly operated by a user, without robotic control. The endoscope assembly may include active steering (e.g., via teleoperated or manually operated steering wires) or passive steering (e.g., steered by moving along a guide wire or by interaction with the body lumen sidewall). The visualization system 110 may be implemented as hardware in combination with firmware or software which interacts with or is otherwise executed by one or more computer processors, which may include the processor(s) of a control system 116.

A display system 111 displays an image of the surgical site, and any surgical instruments at the surgical site, captured by the visualization system 110. The display 111 and the master control device(s) 112 may be oriented such that the relative positions of the imaging device in the endoscope assembly and the surgical instruments are similar to the relative positions of the surgeon's eyes and hand(s) so the operator can manipulate the surgical instrument 104 and the master control device(s) 112 as if viewing the workspace in substantially true presence. True presence means that the displayed tissue image appears to an operator as if the operator was physically present at the imager location and directly viewing the tissue from the imager's perspective.

Alternatively or additionally, display system 111 may present images of the surgical site recorded and/or modeled preoperatively using imaging technology such as computerized tomography (CT), magnetic resonance imaging (MM), fluoroscopy, thermography, ultrasound, optical coherence tomography (OCT), thermal imaging, impedence imaging, laser imaging, nanotube X-ray imaging, or the like. The presented preoperative images may include two-dimensional, three-dimensional, or four-dimensional (including e.g., time based or velocity based information) images.

In some embodiments, the display system 111 may display a virtual navigational image in which the actual location of the surgical instrument is registered (e.g., dynamically referenced) with preoperative or concurrent images to present the surgeon S with a virtual image of the internal surgical site at the location of the tip of the surgical instrument.

In other embodiments, the display system 111 may display a virtual navigational image in which the actual location of the surgical instrument is registered with prior images (including preoperatively recorded images) or concurrent images to present the surgeon S with a virtual image of a surgical instrument at the surgical site. An image of a portion of the surgical instrument may be superimposed on the virtual image to assist the surgeon controlling the surgical instrument.

Display system 111 may display various combinations of one or more of these real or virtual images to surgeon S. And, in various implementations surgeon S can select which of these one or more real or virtual images are displayed.

As shown in FIG. 1, a control system 116 includes at least one processor (not shown), and typically a plurality of processors, for effecting control between the slave surgical manipulator assembly 102, the master assembly 106, the visualization system 110, and the display system 111. The control system 116 also includes programmed instructions (e.g., a computer-readable medium used to store the instructions) to implement some or all of the methods described herein. While control system 116 is shown as a single block in the simplified schematic of FIG. 1, the system may comprise a number of data processing circuits (e.g., on the slave surgical manipulator assembly 102 and/or on the master assembly 106), with at least a portion of the processing optionally being performed adjacent the slave surgical manipulator assembly, a portion being performed the master assembly, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 116 supports wireless communication protocols such as Bluetooth, IrDA, HomeRF, IEEE 802.11, DECT, and Wireless Telemetry.

In some embodiments, control system 116 may include one or more servo controllers to provide force and torque feedback from the surgical instruments 104 to one or more servomotors for the corresponding control device(s) 112. The servo controller(s) may also transmit signals instructing manipulator assembly 102 to move instruments which extend into an internal surgical site within the patient body via openings in the body. Any suitable conventional or specialized servo controller may be used. A servo controller may be separate from, or integrated with, manipulator assembly 102. In some embodiments, the servo controller and manipulator assembly are provided as part of a robotic arm cart positioned adjacent to the patient's body.

Each manipulator assembly 102 supports a surgical instrument 104 and may comprise a serial kinematic chain of one or more non-servo controlled links (e.g., one or more links that may be manually positioned and locked in place, generally referred to as a set-up structure) and a robotic manipulator. The robotic manipulator assembly 102 is driven by a series of actuators (e.g., motors). These motors actively move the robotic manipulators in response to commands from the control system 116. The motors are further coupled to the surgical instrument so as to advance the surgical instrument into a naturally or surgically created anatomical orifice and to move the distal end of the surgical instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulatable end effector of the instrument for grasping tissue in the jaws of a biopsy device or the like.

Figure 2:
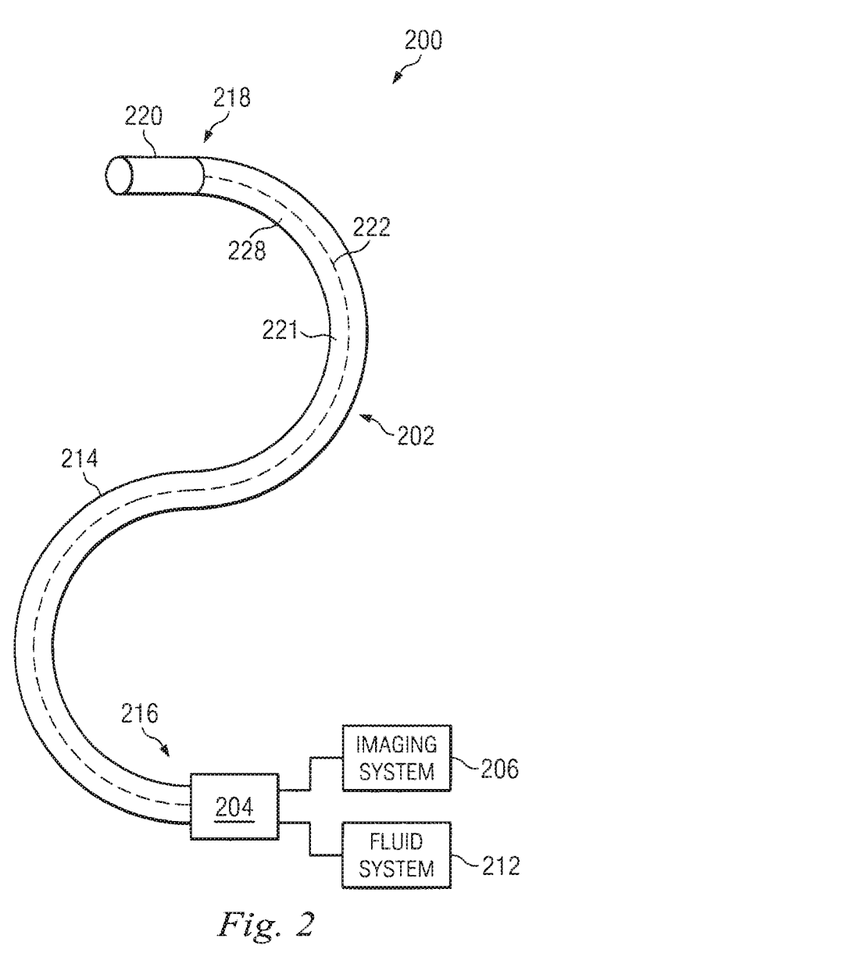
FIG. 2 illustrates an endoscopy system utilizing aspects of the present disclosure.

FIG. 2 illustrates an endoscopy system 200 that incorporates aspects of the present disclosure. The endoscopy system 200 may be incorporated into a robotic surgical system, such as system 100 (e.g., as part of instrument 104), as part of the visualization and display system. Alternatively, the endoscopy system 200 may be used for non-robotic exploratory procedures or in procedures involving traditional manually operated surgical instruments, such as laparoscopic instruments. The system 200 includes an endoscopic probe 202 coupled by an interface unit 204 to an imaging system 206, a fluid system 212, and other optional support systems (not shown), as deemed beneficial. The endoscopic probe 202 includes an elongated flexible body 214 having a proximal end 216 and a distal end 218. In one embodiment the flexible body 214 has an approximately 2 mm outer diameter. Other flexible body 214 outer diameters may be larger or smaller. The flexible body 214 may be formed from a transparent, semi-transparent, or opaque material. The probe 202 also includes a support member 220 coupled to the distal end 218 of the flexible body 214. Further details of the support member 220 are described in detail below for FIGS. 3-6.

The flexible body 214 includes a channel 221 that runs longitudinally along at least a portion of the length of the flexible body, and in which an image capture instrument 222 extends. Optionally, other operational components 224 may extend within the channel 221. (See FIG. 3) In one aspect, the remaining portion of the channel 221, not occupied by the instrument 222 or any other operational components, is a flow channel 228. Alternatively, the flow channel may be a discrete channel (e.g., a tubular member) extending through the flexible body 214.

In some implementations, image capture instrument 222 includes a stereoscopic or monoscopic camera at or near the distal end 218 of the flexible body 214 or within the support member 220. This camera is used for capturing images that are then transmitted to and processed by the imaging system 206 for display. The image capture instrument 222 includes a cable 223 (see FIGS. 4, 5A, and 6) coupled to the camera for transmitting the captured image data to the imaging system 206. Alternatively, the image capture instrument may be a coherent fiber-optic bundle, such as a fiberscope, that couples to the imaging system, in which case the camera is located away from the distal end of the endoscopic system. The image capture instrument may be single or multi-spectral, for example capturing image data in the visible spectrum, or capturing image data in the visible and infrared or ultraviolet spectrums.

The optional operational components 224 may include illumination components or steering controls, such as cables or other mechanical components to controllably bend the distal end of the flexible body. The flexible body 214 may be steerable or, alternatively, may be non-steerable with no integrated mechanism for operator control of the instrument bending. The flexible body 214 may further house control mechanisms (not shown) for operating a surgical end effector or another working distal part that is manipulable for a medical function, e.g., for effecting a predetermined treatment of a target tissue. For instance, some end effectors have a single working member such as a scalpel, a blade, or an electrode, and this working member may or may not have an associated mechanical degree of freedom (e.g., a movable electrocautery electrode). Other end effectors may include pair or plurality of working members such as forceps, graspers, scissors, or clip appliers, for example, and often at least one mechanical degree of freedom is associated with these working members (e.g., a jaw that closes against an opposing jaw). Examples of electrically activated end effectors include electrosurgical electrodes, transducers, sensors, and the like.

The flow channel 228 provides a flow pathway between the fluid system 212 and the support member 220 to, for example, convey an irrigation fluid to the surgical site, deliver a medication (therapeutic agent) to the surgical site, provide gas insufflation, provide suction at the surgical site, extract biopsied tissue, or the like. The fluid system 212 may include pumps, fluid reservoirs, and other components for delivering or receiving fluids via the flow channel 228. In aspects in which the flow channel 228 is the portion of channel 221 not otherwise occupied, fluid (e.g., gas or liquid) or other flowable material (e.g., granular medication/therapeutic material, gel, mucus, or tissue) flows around and in contact with the image capture instrument 222 and/or the one or more other operational components 224. In this aspect, the image capture instrument 222 and operational components 224 may be individually or collectively shielded, insulated, or otherwise protected from the surrounding fluid.

Figure 3:
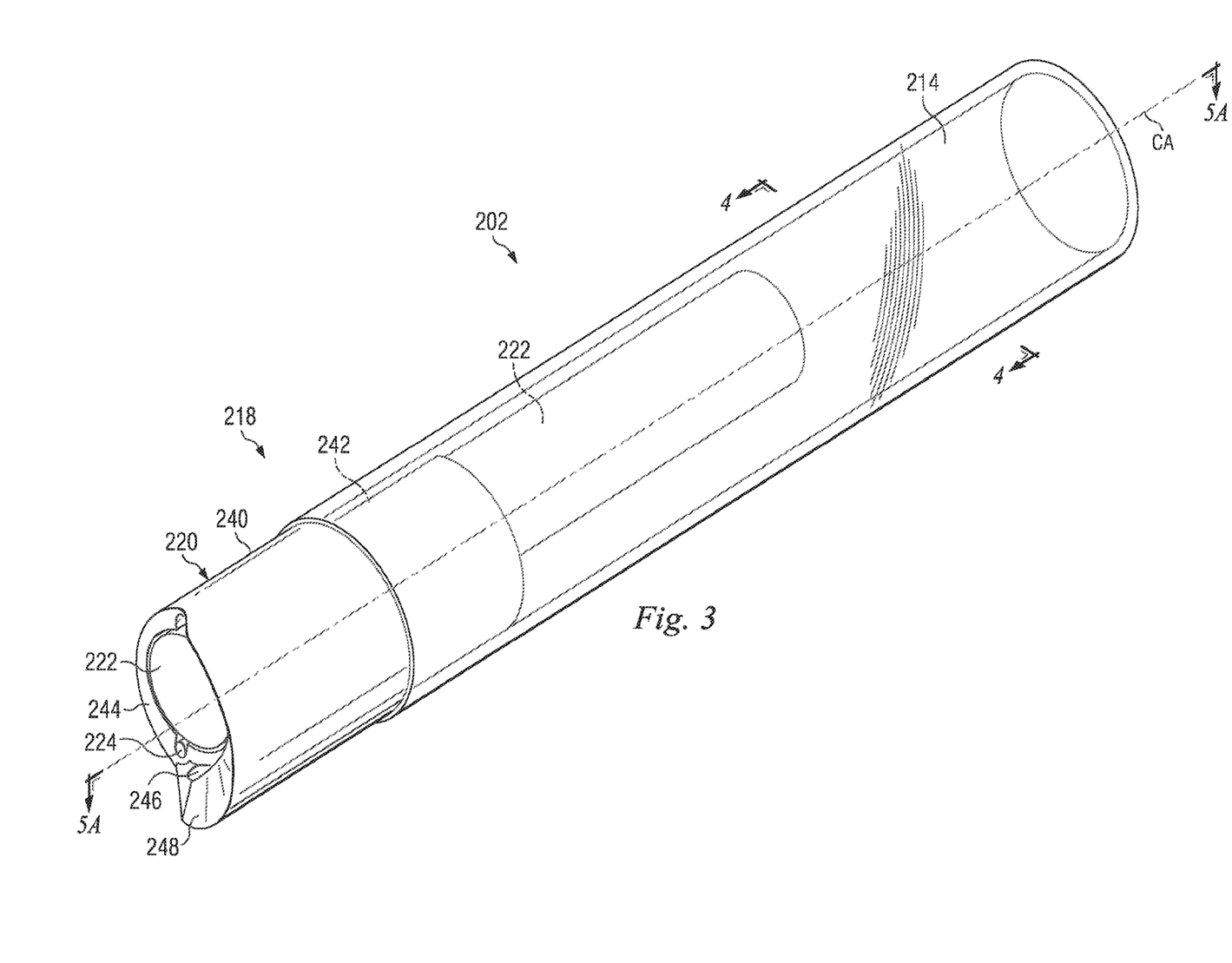
FIG. 3 is an illustration of a distal end of an endoscopic probe according to an embodiment of the present disclosure.

FIG. 3 is an illustration of the distal end 218 of endoscopic probe 202. The support member 220 includes a distal cylindrical wall portion 240 integrally formed with a partially cylindrical proximal wall portion 242. The wall portion 240 is defined as the portion of the support member 220 outside of the flexible body 214, and the wall portion 242 is defined as the portion of the support member 220 inside the flexible body 214. The wall portion 242 may have an outer radius smaller than the outer radius of the wall portion 240 so that the outer diameter of the distal end of flexible body 214 and wall portion 240 are effectively the same. Alternatively, wall portions 240, 242 may have a common, continuous outer radius sized to fit within the channel 221 of the flexible body 214. In various other embodiments, the wall portion 242 may be a fully cylindrical wall with a continuous common outer diameter with portion 240. In some embodiments, the outer diameter of wall portion 240 may be larger than the inner diameter of the channel 221 of the flexible body 214, and the outer diameter of the wall portion 242 is sized to fit within the channel 221 of the flexible body 214. When the wall portion 242 is inserted into the flexible body 214, the wall portion 240 abuts the flexible body to limit the distance the support member 220 may be inserted into the flexible body. In various other embodiments, the inner diameter(s) of wall portion(s) 240 and/or 242 may be sized to allow the distal end of the flexible body 214 to fit within or abut wall portion(s) 240 and/or 242. In various other alternative embodiments where the wall portion 242 is partially cylindrical, the wall portion 242 may be approximately half or three-quarter cylindrical (e.g., C-shaped when viewed in cross-section).

The support member 220 may be formed of a biologically compatible material including plastics, metals, and/or ceramics. For example, the support member 220 may be a molded or extruded construction. The support member 220 may be bonded, friction fit, mechanically secured, or otherwise coupled to the flexible body 214. In various embodiments, the support member may include an articulable nozzle or director portion that is movable relative to the other portions of the support member.

Figure 4:
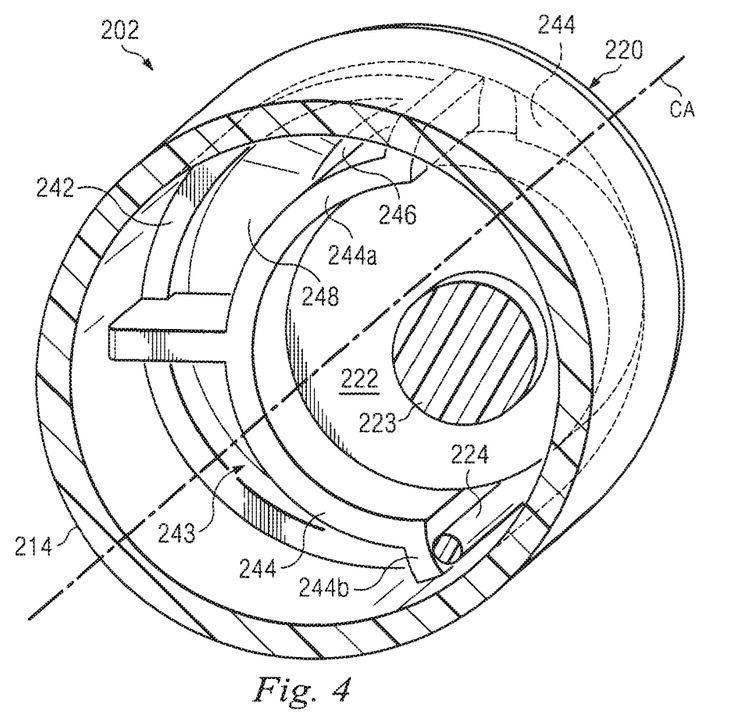
FIG. 4 is a cross-sectional perspective view of the endoscopic probe of FIG. 3 as viewed from location of the cross-section toward the distal end of the probe, taken along cut line 4-4 in FIG. 3.
Figure 5:
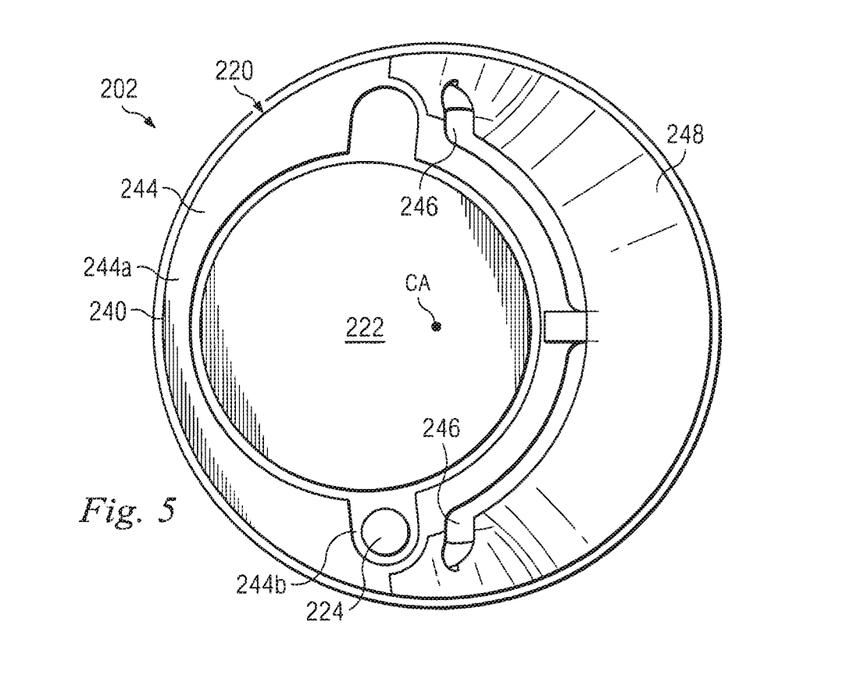
FIG. 5 is a distal end view of the endoscopic probe according to the embodiment of FIG. 3.
Figure 5A:
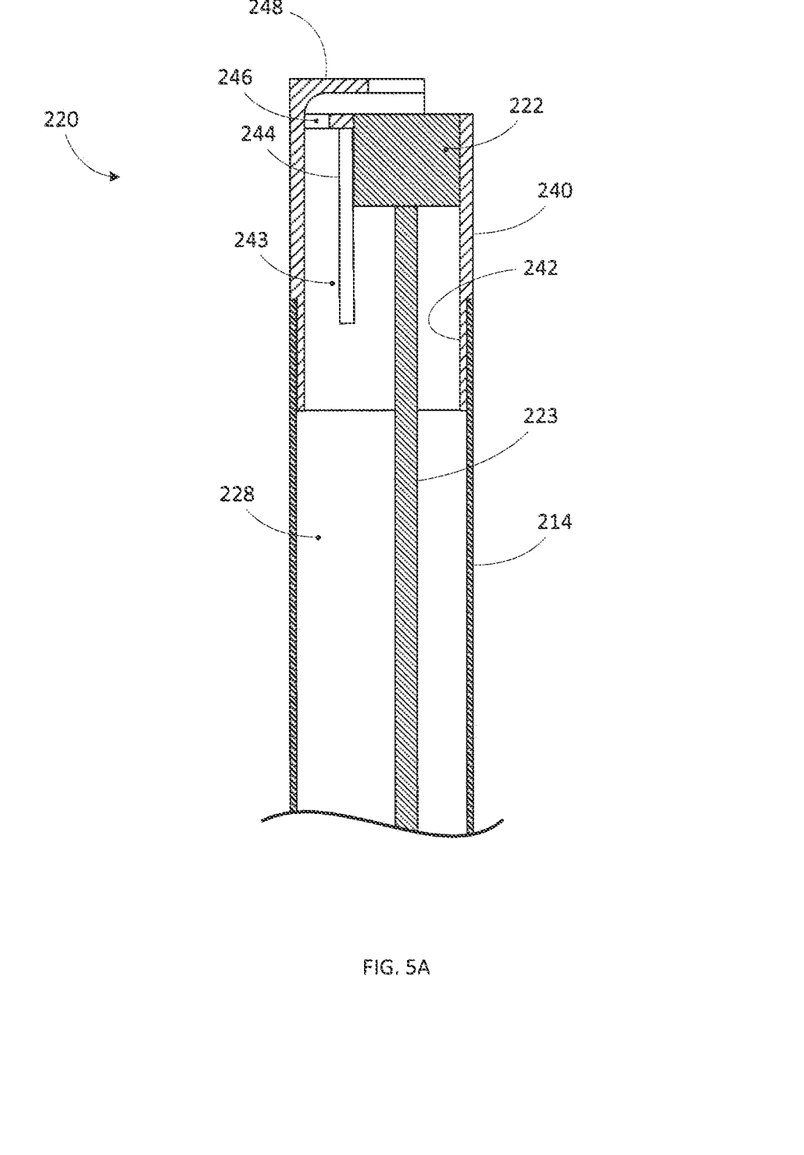
FIG. 5A is a cross-sectional view of the endoscopic probe according to the embodiment of FIG. 3.
Figure 6:
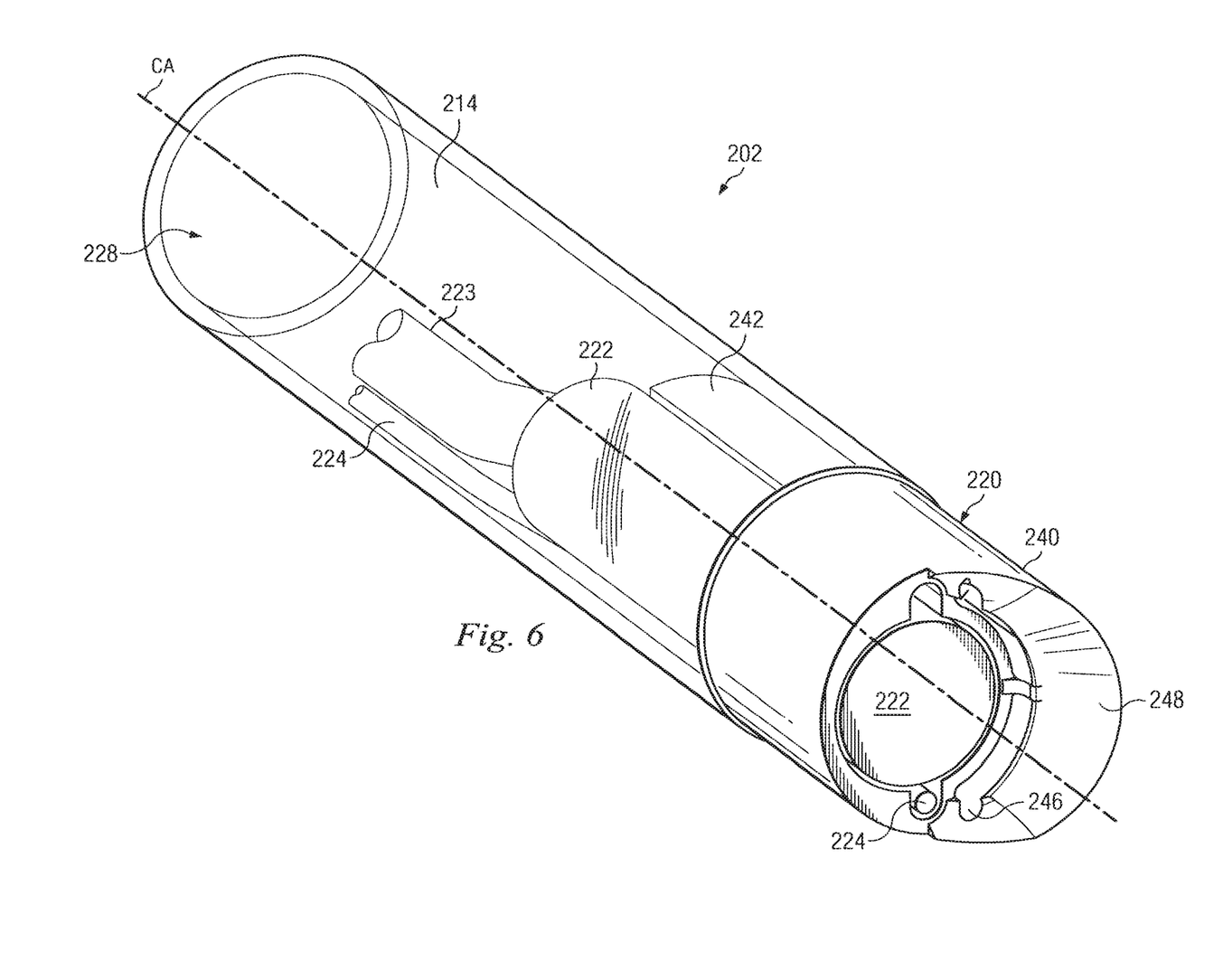
FIG. 6 is an illustration of a distal end of the endoscopic probe according to the embodiment of FIG. 3.

The support member 220 is shown in greater detail in FIGS. 4, 5, 5A, and 6. More specifically, FIG. 4 illustrates a cross-sectional view of the distal end of the endoscopic probe 202 as viewed from a cross-section of the flexible body 214 toward the distal end of the support member 220. FIG. 5 is a distal end view of the support member 220. FIG. 5A is a simplified cross-sectional view of support member 220 (indicated by the dashed section line in FIG. 4). FIG. 6 is a side view of the distal end of the endoscopic probe 202.

The support member 220 further includes an interior channel 243 bounded by the wall portions 240, 242 and an optional frame 244 extending within the interior channel 243. As assembled, in one aspect the interior channel 243 of the support member 220 is in communication with the channel 221 of the flexible body 214. In other aspects in which flow channel 228 is a discrete channel, then the discrete channel is in communication with interior channel 243. The frame 244 may be integrally formed with (e.g., molded or extruded) or otherwise attached to one or more of the wall portions 240, 242. The image capture instrument 222 and other operational components 224 (if any) extending through the flexible body 214 are further extended into the support member 220, where they can be aligned relative to each other and retained by the frame 244. The frame 244 may generally restrict the lateral movement of the image capture instrument and the other operational components, maintaining their relative alignment while permitting a limited amount of rotational or longitudinal movement. Alternatively, the image capture instrument and other operational components may be affixed to the frame 244 to prevent either or both translational or rotational movement. Alternatively, the components may be affixed to and/or positioned within openings in the distal face of support member 220.

In the depicted embodiment, the frame 244 includes a section 244a sized and shaped to receive the image capture instrument 222 and to limit or prevent movement of the image capture instrument within the interior channel 243. The frame 244 may also include one or more sections 244b, sized and shaped to receive various operational components 224 to limit or prevent movement of the operational components within the interior channel 243. If no operational components are used, the frame sections 244b are unnecessary. In this embodiment, the image capture instrument 222 is retained by the frame 244 in a position laterally displaced from a central longitudinal axis CA of the support member 220. In alternative embodiments, the frame 244 may retain the image capture instrument and any operational components in different arrangements relative to each other and/or the walls of the support member.

The area of the interior channel 243 not occupied by the frame 244, the image capture instrument 222, or other structures, can serve as a flow passageway in communication with flow channel 228 of the flexible body 214. This design can maximize the effective fluid flow path cross section, thereby beneficially reducing the pressure required to create a desired fluid flow rate through (and out of) probe 202. The support member 220 has one or more distal openings 246 (one is visible in FIG. 3, see FIG. 5 showing two) and one or more fluid directors 248 (one is shown) that extend inward from the cylindrical wall portion 240 to angle, curve, or otherwise direct or deflect flow from the distal opening towards the image capture instrument 222. The fluid director may include grooves, channels, protrusions, or other physical features to further direct, deflect, or agitate the passing fluid. In the depicted embodiment, the fluid director 248 extends inward toward longitudinal axis CA from a side of the wall portion 240 opposite from the laterally displaced position of image capture instrument 222. As described in further detail below, the fluid director 248 serves to direct fluid conveyed through the flexible body 214 and support member 220 toward the image capture instrument 222 to rinse away accumulated blood, tissue, or other matter that obstructs instrument 222's imaging capability. Fluid director 248 is angled and/or shaped so that the directed fluid flows across the distal end of instrument 222 to carry unwanted matter from instrument 222's distal end.

Note that while depicted as an integral, lip-like structure for exemplary purposes, fluid director 248 can take any form that can direct fluid conveyed from within flexible body 214 toward image capture instrument 222, such as one or more internal directional passages (i.e., fluid pathways within support member 220) or a separate cap or clip fitted on support member 220. Note further that while distal opening 246 is depicted as a single opening positioned to the side of image capture instrument 222 for exemplary purposes, distal opening 246 may be any number of openings in any arrangement relative to image capture instrument 222 (e.g., multiple openings positioned around the distal end of image capture instrument 222). In such multiple opening 246 aspects, each opening may be associated with a corresponding fluid director 248, two more openings may be associated with a single fluid director 248, and/or one or more openings may not be associated with a fluid director 248. For example, in one illustrative embodiment several openings 246 surround the distal end of image capture instrument 222, and only openings on one side of instrument 222 are associated with a fluid director, so that fluid generally flows from one side of the distal end of instrument 222 to the other.

The support member 220 can also maintain the relative alignment of the image capture instrument 222 and any operational components 224. Because the components can be all held in alignment within the channel 221 of the flexible body 214 by the support member 220, a separate and distinct fluid channel or a separating wall within the flexible body 214 is not required. This construction leaves all remaining space within the channel 221 of the flexible body 214 and the channel 243 of the support member 220 for fluid passage to, for example, convey an irrigation fluid, deliver a medication/therapeautic, provide insufflation, provide suction, extract biopsied tissue, or the like. The maximized flow passageway cross section relative to the overall cross section of the channel 221 can, with reference to the flexible body's outer diameter, minimize flow resistance and pressure drop along the length of the flexible body 214. Furthermore, the absence of a discrete fluid channel or wall within the flexible body 214 eliminates any additional stiffness that such a wall or channel would contribute to the flexible body. Thus, the flexible body 214 has a higher degree of flexibility than it would otherwise have if occupied by a discrete fluid channel. In some embodiments, because the rigid support member 220 extends a relatively short distance into the distal end of the flexible body 214, it imparts rigidity to only the distal end of the flexible body 214, allowing the remaining length of flexible body 214 to maintain a high degree of flexibility. The probe 202 may be a single use device or may be designed for sterilization (e.g., chemical, autoclave) and multiple uses.

Figure 7:
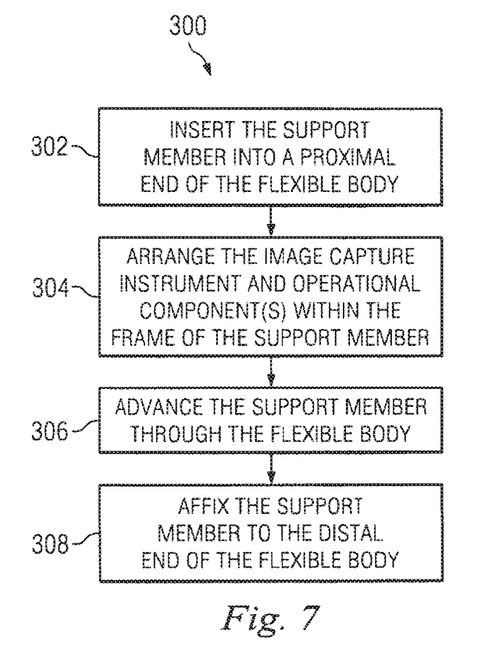
FIG. 7 is flow chart describing a method of assembling an endoscopic probe according to an embodiment of the disclosure.

A method of manufacturing the endoscopic probe 202 is provided at FIG. 7 and includes, at 302, inserting the support member 220 into a proximal end of the flexible body 214. At 304, the image capture instrument 222 and any operational components 224 are arranged in the frame. At 306, the support member 220 is advanced through the flexible body 214 toward the distal end of the flexible body 214. As shown in FIGS. 3 and 6, the outer wall portion 240 may be advanced through the distal opening of the flexible body 214. In some embodiments, flexible body 214 can exhibit sufficient radial elasticity to allow outer wall portion 240 to be advanced through the interior of flexible body 214 and/or outer wall portion 240 can be sized to be able to pass through the interior of flexible body 214 without, or with minimal, radial stretching of flexible body 214. At 308, the inner wall portion 242 is affixed to the flexible body 214. In one aspect, this method of manufacturing may be particularly suitable for embodiments in which the inner wall portion 242 and the outer wall portion 240 have a common outer diameter. It may also be suitable for embodiments in which the diameter of the outer wall portion 240 is larger than the inner wall portion 242.

An alternative method of manufacturing may include inserting the support member 220 into the channel 221 of the flexible body 214 through the distal end. Where the outer diameter of the wall portion 240 is larger than the inner diameter of the channel 221, the support member 220 is advanced through the distal end of the flexible body 214 until the wall portion 240 abuts the flexible member 214.

Figure 8:
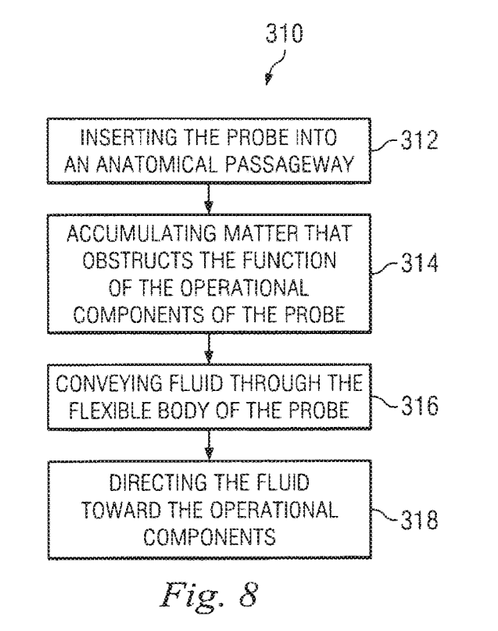
FIG. 8 is a flow chart describing a method of using an endoscopic probe according to an embodiment of the disclosure.

A method of using the endoscopic probe 202 is provided at FIG. 8 and includes, at 312, inserting the probe into an anatomical passageway of a patient. At 314, as the probe is advanced through the patient, blood, tissue, mucous, or other matter accumulates on one or more of the image capture instrument 222 and other operational components 224 and obstructs their function. For example, matter accumulated on the image capture instrument 222 may block all or part of the camera's field of view and make capturing a usable image impossible. Therefore, at 316, to clean the image capture instrument 222, a fluid (e.g., a saline solution, a gas) is conveyed distally through the flow channel 228 of the flexible body 214 and through the remaining flow passageway of the interior channel 243 of the support member 220. As the conveyed fluid flows distally through flexible body 214 and support 220, it flows generally around and in contact with the image capture instrument 222. At 318, the fluid reaches the distal end of support 220, at which point it impacts the fluid director 248. At a result of this impact, the fluid is directed toward and across the distal end of the image capture instrument 222 so that the fluid contacts and flows across the distal end of image capture instrument 222. The deflected fluid thus cleans the image capture instrument 222, ridding it of blood, mucous, tissue, or other material that may have accumulated and enabling instrument 222 to once again provide usable images. In alternative embodiments, multiple fluid directors may be used to direct the flow of fluid. In another embodiment, the fluid director can additionally or alternatively direct suctioned fluid or fluid with particulate matter (e.g. blood, tissue, saline, air) across the image capture instrument 222 to dislodge accumulated material. In another embodiment, the fluid director can additionally or alternatively be used to direct the delivery of a fluid or other flowable material toward a particular direction in the anatomical passageway. For example, one or more fluid director 248 may be positioned and configured to direct fluid in various directions outward and in front of, to the side of, or behind the distal end of probe 202.

In various other aspects of the invention, which may be combined with any other aspect described herein, active fluid flow can be used to cool image capture instrument 222, or elements of image capture instrument 222. Thus, a single fluid can be used for both cooling and one or more other purposes, such as cleaning as described above. For example, in an embodiment depicted in FIG. 11, an image signal processor (ISP) 225 (optionally including a charge-coupled device (CCD) or complementary metal-oxide-semiconductor (CMOS) sensor and associated electronics) in image capture instrument 222 is depicted. During operation of image capture instrument 222, it is desirable to dissipate heat generated by ISP 225 (and any nearby components) to ensure accurate imaging performance. Fluid flow in a proximal to distal direction (indicated by the bold arrow) over image capture instrument 222 can beneficially be used to provide at least some of this heat dissipation. Note that in some embodiments, this fluid flow can alternatively or additionally be directed over portions of image capture instrument 222 exposed to the exterior of probe 202 (e.g., the lens or distal tip of image capture instrument 222) to provide cooling to those portions or even the distal end of probe 202.

Figure 11:
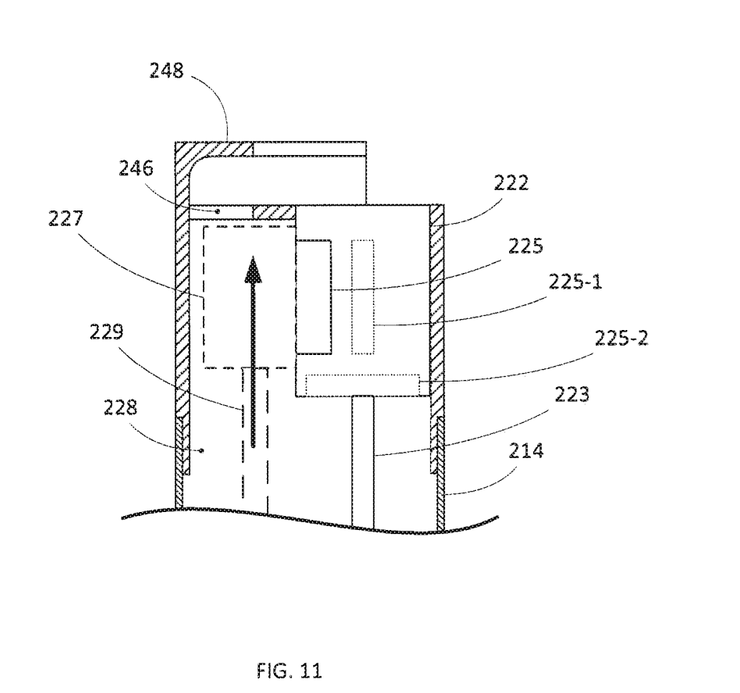
FIG. 11 is an illustration of a cross-section of a distal end of an endoscopic probe incorporating active cooling of an image capture instrument or other heat-generating component.

For example, ISP 225 can be positioned at or adjacent an outer surface of image capture instrument 222, thereby allowing any generated heat to be carried away by the moving fluid. In some embodiments, the fluid can be a gas, such as nitrogen or carbon dioxide. In some embodiments, the gas can be delivered directly to and/or into image capture instrument 222 via an optional dedicated cooling fluid channel 229. In some other embodiments, the same gas used for patient insufflation (typically carbon dioxide) can be used for cooling ISP 225, thereby beneficially reducing the need for dedicated cooling gas delivery mechanisms. In addition, the resultant warming of the insufflation gas as it flows by ISP 225 can in some instances reduce or eliminate the need for the dedicated warming devices often used to raise the temperatures of insufflation gases prior to introduction into a patient. Furthermore, the combined use of the gas delivered through the flow path for insufflation and for cooling can in some instances eliminate the need for a dedicated cooling gas return flow path within probe 202, thereby reducing mechanical complexity and/or size of the probe design. And, continually directing the gas across the distal end of instrument 222 helps to keep foreign material away from, or remove it from, the distal end of instrument 222. In an additional aspect, fluid flow velocity can be increased from time to time as necessary to provide an additional cleaning function. In this illustrative implementation, therefore, a single fluid can be used to provide cooling for a component at the distal end of an instrument, to provide cleaning for this or another distal end component, and to provide a useful function at the surgical site.

In other embodiments, the fluid can be a liquid, such as water or saline. In some embodiments, the cooling liquid can be delivered directly to and/or into image capture instrument via optional dedicated cooling fluid channel 229. In some other embodiments, the same fluid used for flushing/cleaning the external lens of image capture instrument 222 (as described above) can be used for cooling ISP 225, thereby beneficially reducing the need for a dedicated cooling liquid delivery system. Furthermore, the combined use of the liquid delivered through the flow path for lens cleaning and for cooling can in some instances eliminate the need for a dedicated cooling liquid return flow path within probe 202, thereby reducing mechanical complexity and/or size of the probe design.

Although depicted as being positioned at or adjacent to the exterior of image capture instrument 222 for exemplary purposes, in various other embodiments ISP 225 can be positioned anywhere within image capture instrument 222, as indicated by optional alternative positions 225-1 and 225-2 (indicated by dotted lines). If ISP 225 is positioned at a distance from an exterior surface of image capture instrument 222, in some embodiments additional thermal conduction elements can be incorporated into image capture instrument 222 to improve heat transfer from ISP 225 to the cooling fluid. For example, heat pipes, thermally conductive structures (e.g., copper, gold, or aluminum plates, rods, or shims), and/or thermally conductive fillers (e.g., epoxies or potting materials), among others, can provide effective thermal pathways from ISP 225 to the exterior of image capture instrument 222 so that heat can be carried away by the cooling fluid. For therapeutic use, where necessary such thermal conduction elements are either biocompatible or are biocompatibly insulated to avoid possible patient harm.

In various other embodiments, an optional supplemental heat exchange element 227 can be coupled to image capture instrument 222 to enhance heat transfer to the cooling fluid. For example, heat exchange element 227 can be one or more heat spreaders, finned heat sinks, heat pipes, or any other structure/system for transferring heat from image capture instrument 222 to the cooling fluid. In various embodiments, heat exchange element 227 can be mounted on the exterior of image capture instrument 222, mounted directly against ISP 225 (e.g., through the exterior of image capture instrument 222), or integrated into the exterior of image capture instrument 222 (e.g., fins or ridges formed in a metal housing for image capture instrument 222).

Figure 9:
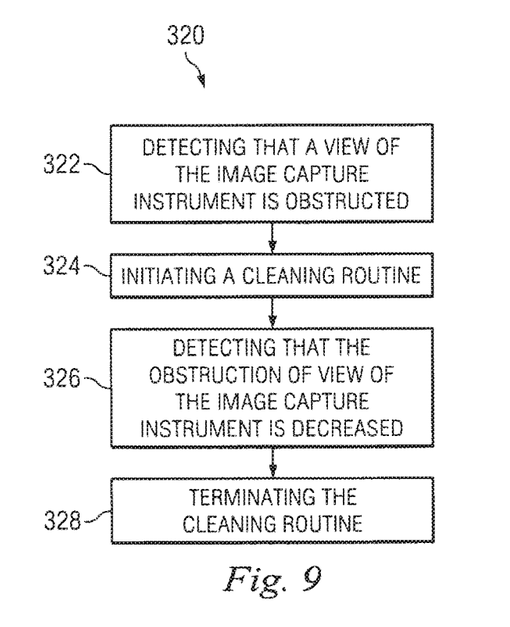
FIG. 9 is a flow chart describing a method of cleaning an endoscopic probe according to an embodiment of the disclosure.
Figure 10:
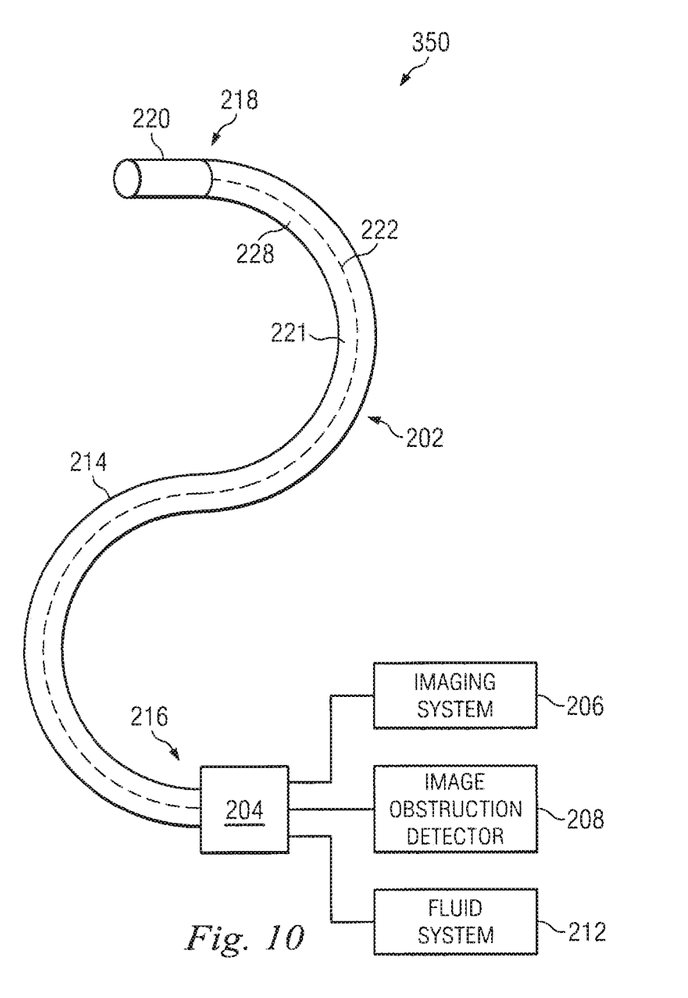
FIG. 10 illustrates another endoscopy system utilizing aspects of the present disclosure.

A method 320 of cleaning the endoscopic probe 202 is provided at FIG. 9. FIG. 10 illustrates an endoscopy system 350 using aspects of the present disclosure. The system 350 is similar to the system 200 and further includes an image obstruction detector 208, which includes software and/or hardware with programmed instructions for detecting whether the view of the image capture instrument 222 is obstructed. It should be understood that information and commands may be exchanged between the imaging system 206, image obstruction detector 208, and fluid system 212 in order to carry out the automated cleaning aspects.

The method 320 includes, at 322, detecting with the image obstruction detector 208 that a view of the image capture instrument 222 is obstructed. The detection may occur when a received image from the image capture instrument 222 shows blood, tissue residue, mucous, or other body matter attached to the distal end of the image capture instrument or another portion of the probe 202 obstructing the view of the image capture instrument. Alternatively, the probe 202 may include an optical or other type of sensor which provides an indication that a view of the image capture instrument is obstructed. The detection process may further include determining whether the level of obstruction exceeds a predetermined limit. For example, a view obstructed by less than a predetermined limit of 10 percent of the view area may not require the initiation of the cleaning routine. The predetermined limit may be increased to allow more debris to accumulate between automatic cleaning routines, or the predetermined limit may be decreased, thereby increasing the frequency of automatic cleanings. The predetermined limit may be effectively zero percent, in which case, any obstruction of the view will initiate the cleaning routine. In one example, an obstruction may be detected when a predetermined percentage (e.g., 25 percent or 50 percent) of the pixels of the camera are dark (i.e., at least some threshold portion of the lens is occluded). In another example, an obstruction may be detected when an average pixel value is less than a predetermined minimum intensity (i.e., overall brightness is reduced because transmission is reduced). In another example, an obstruction may be detected based on the pixel brightness differential across pixels in a contiguous area. A low intensity differential may indicate that the camera is blocked. Two or more of these detection methods may be combined in some implementations to provide an enhanced detection method.

At 324, a cleaning routine is automatically initiated when the image obstruction threshold is exceeded. The cleaning routine may include activating the control system to dispense a fluid from the fluid system 212 to carry away the obstructing body matter, as described above. Alternatively the cleaning routine may include providing a cue to a user to manually activate the fluid system 212 to carry away the obstructing matter. Such a cue may be, for example, auditory (e.g., a tone) or visual (e.g., a message displayed on a display screen of display system 111).

At 326, the method includes detecting that the obstruction of the view of the image capture instrument has been removed entirely or has been decreased to a level below the predetermined limit. At 328, responsive to the detection of the decreased obstruction, the cleaning routine is terminated by activating the control system to cease the dispensing of fluid or to cue the user to manually terminate the dispensing of fluid. In alternative embodiments, the cleaning routine may be terminated after a predetermined length of time or after a predetermined amount of fluid is dispensed, with or without regard to whether the obstruction has been decreased or removed. In some implementations, a series of two or more automated detect-clean routines is performed until either the system senses that the obstructing matter is carried away or a predetermined number of cleaning routines has been completed, in which case an alternate cleaning method would be required, such as withdrawing the flexible body 214 from the surgical site for manual cleaning. The cleaning system may in some cases output a message on display 111 that advises the surgeon that the automated cleaning process has not been completed or effective. The surgeon may then decide to continue using the probe with the vision as-is, or the surgeon may choose to withdraw the probe for cleaning.

Although the systems and methods have been described herein with respect to endoluminal probes, the systems and methods are also suitable for other applications in which in vivo cleaning of an instrument is advantageous. For example, the fluid delivery and cleaning systems and methods described may be suitable for use with ablation catheters, laser fibers, other minimally invasive instruments, or other types of endoscopic devices.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An anatomical probe system, comprising:
   an elongated flexible body including a channel defined by a wall;
   an operational component extending within the channel of the elongated flexible body;
   a support member at a distal end of the elongated flexible body, wherein the support member comprises:
   a curved wall having a portion sized to fit within the channel of the elongated flexible body; and
   a frame shaped to retain the operational component and including a frame wall coupled to the curved wall such that the frame wall and the portion of the curved wall sized to fit within the channel form an enclosed interior channel, wherein the frame wall overlaps the portion of the curved wall sized to fit within the channel of the elongated flexible body in an axial direction with respect to a central longitudinal axis of the support member such that a plane transverse to the central longitudinal axis intersects both the frame wall and the portion of the curved wall, and wherein the enclosed interior channel is in fluid communication with the channel of the elongated flexible body;
   an image obstruction detector configured to detect an obstruction of a view of the operational component and initiate a cleaning routine in response to the detection of the obstruction; and
   a fluid director disposed on the support member, wherein the fluid director is configured to receive fluid conveyed through the channel, wherein a portion of the fluid contacts and is confined by the wall, and into contact with the fluid director to direct the fluid toward the operational component.

2. The anatomical probe system of claim 1 wherein the operational component comprises an image capture instrument.

3. The anatomical probe system of claim 2 wherein the image obstruction detector is further configured to detect a decrease in the obstruction of the view of the operational component and terminate the cleaning routine in response to the detected decrease in the obstruction.

4. The anatomical probe system of claim 1 wherein the operational component comprises an illumination device.

5. The anatomical probe system of claim 1 further comprising a fluid conveyance system from which the fluid is conveyed.

6. The anatomical probe system of claim 5 wherein the channel and the operational component are configured such that a portion of the fluid conveyed from the fluid conveyance system is conveyed into contact with the operational component within the elongated flexible body.

7. The anatomical probe system of claim 5 wherein the fluid conveyance system is configured to provide an irrigation fluid.

8. The anatomical probe system of claim 5 wherein the fluid conveyance system is configured to provide suction.

9. The anatomical probe system of claim 5 wherein the fluid conveyance system is configured to cool the operational component with the fluid.

10. An anatomical probe system, comprising:
- an elongated flexible body including a channel defined by a wall;
- an operational component extending within the channel of the elongated flexible body;
- a support member at a distal end of the elongated flexible body, the support member supporting a portion of the operational component;
- an image obstruction detector configured to:
  - detect an obstruction on a lens of the operational component by determining that the obstruction exceeds a predetermined limit and initiate a cleaning routine in response to the detection of the obstruction; and
  - detect a decrease in the obstruction of the operational component and terminate the cleaning routine in response to the detected decrease in the obstruction; and
- a fluid director disposed on the support member, wherein the fluid director is configured to receive fluid conveyed through the channel and into contact with the fluid director to direct the fluid toward the operational component during the cleaning routine.

11. The anatomical probe system of claim 10 wherein the support member comprises:
- a curved wall sized to fit within the channel of the elongated flexible body; and
- a frame shaped to retain the operational component and including a frame wall coupled to the curved wall such that the curved wall and the frame wall form an enclosed interior channel, wherein the enclosed interior channel is in fluid communication with the channel of the elongated flexible body, and wherein the fluid director extends from the curved wall toward the frame.

12. The anatomical probe system of claim 11 further comprising a second operational component aligned with the operational component, wherein the frame includes a frame section shaped to receive the operational component and prevent movement of the second operational component relative to the operational component.

13. The anatomical probe system of claim 10 further comprising a fluid conveyance system from which the fluid is conveyed.

14. The anatomical probe system of claim 13 wherein the fluid conveyance system is configured to provide an irrigation fluid.

15. The anatomical probe system of claim 13 wherein the fluid conveyance system is configured to provide suction.

16. The anatomical probe system of claim 13 wherein the fluid conveyance system is configured to cool the operational component with the fluid.

17. The anatomical probe system of claim 10 wherein the operational component is coupled to the support member to prevent at least one of rotational or lateral movement of the operational component.

18. The anatomical probe system of claim 10, wherein the operational component comprises an image capture instrument.

19. The anatomical probe system of claim 10, wherein the support member includes a frame sized and shaped to receive the operational component.

* * * * *